(12) United States Patent
McKay

(10) Patent No.: US 8,475,824 B2
(45) Date of Patent: Jul. 2, 2013

(54) RESORBABLE MATRIX HAVING ELONGATED PARTICLES

(75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 501 days.

(21) Appl. No.: 12/693,770

(22) Filed: Jan. 26, 2010

(65) Prior Publication Data

US 2011/0182962 A1 Jul. 28, 2011

(51) Int. Cl.
*A61F 2/00* (2006.01)

(52) U.S. Cl.
USPC .......................................................... 424/423

(58) Field of Classification Search
None
See application file for complete search history.

(56) References Cited

U.S. PATENT DOCUMENTS

| | | |
|---|---|---|
| 4,624,255 A | 11/1986 | Schenck et al. |
| 4,863,457 A | 9/1989 | Lee |
| 5,522,844 A | 6/1996 | Johnson |
| 5,868,789 A | 2/1999 | Huebner |
| 6,069,129 A | 5/2000 | Sandberg et al. |
| 6,179,862 B1 | 1/2001 | Sawhney |
| 6,287,588 B1 | 9/2001 | Shih et al. |
| 6,331,311 B1 | 12/2001 | Brodbeck et al. |
| 6,428,804 B1 | 8/2002 | Suzuki et al. |
| 6,432,063 B1 | 8/2002 | Marcus |
| 6,461,631 B1 | 10/2002 | Dunn et al. |
| 6,491,651 B1 | 12/2002 | Leahy et al. |
| 6,589,549 B2 | 7/2003 | Shih et al. |
| 6,630,155 B1 | 10/2003 | Chandrashekar et al. |
| 6,632,457 B1 | 10/2003 | Sawhney |
| 6,696,073 B2 | 2/2004 | Boyce et al. |
| 6,756,058 B2 | 6/2004 | Brubaker et al. |
| 6,773,714 B2 | 8/2004 | Dunn et al. |
| 6,863,694 B1 | 3/2005 | Boyce et al. |
| 6,974,462 B2 | 12/2005 | Sater |
| 7,144,412 B2 | 12/2006 | Wolf et al. |
| 7,166,570 B2 | 1/2007 | Hunter et al. |
| 7,220,281 B2 | 5/2007 | Lambrecht et al. |
| 7,229,441 B2 | 6/2007 | Trieu et al. |
| 7,235,043 B2 | 6/2007 | Gellman et al. |
| 7,318,840 B2 | 1/2008 | McKay |
| 7,329,259 B2 | 2/2008 | Cragg |
| 7,361,168 B2 | 4/2008 | Makower et al. |
| 7,367,978 B2 | 5/2008 | Drewry et al. |
| 7,449,019 B2 | 11/2008 | Uchida et al. |
| 7,462,155 B2 | 12/2008 | England |
| 7,482,174 B2 | 1/2009 | Kiefer et al. |

(Continued)

FOREIGN PATENT DOCUMENTS

WO 03005961 A2 1/2003

OTHER PUBLICATIONS

U.S. Appl. No. 12/194,432, filed Aug. 19, 2008.
U.S. Appl. No. 12/193,794, filed Aug. 19, 2008.

(Continued)

*Primary Examiner* — Carlos Azpuru
*Assistant Examiner* — Casey Hagopian
(74) *Attorney, Agent, or Firm* — Sorell Lenna & Schmidt LLP

(57) ABSTRACT

Compression resistant matrices and methods are provided that have elongated particles embedded therein. The compression resistant matrices provide improved stability and mechanical strength and resists shifting, extrusion and rotation after implantation. In some embodiments, the matrices provided reduce or prevent surface compression of the implantable matrix which will cause unwanted increased amounts of growth factor (e.g., bone morphogenic protein) to leak from the matrix.

16 Claims, 2 Drawing Sheets

U.S. PATENT DOCUMENTS

| | | |
|---|---|---|
| 2001/0014831 A1 | 8/2001 | Scarborough |
| 2002/0009454 A1 | 1/2002 | Boone et al. |
| 2002/0082694 A1 | 6/2002 | McKay |
| 2002/0090398 A1 | 7/2002 | Dunn et al. |
| 2003/0009235 A1 | 1/2003 | Manrique et al. |
| 2003/0133967 A1 | 7/2003 | Ruszczak et al. |
| 2003/0204191 A1 | 10/2003 | Sater et al. |
| 2003/0236573 A1 | 12/2003 | Evans et al. |
| 2004/0072799 A1 | 4/2004 | Li et al. |
| 2004/0082540 A1 | 4/2004 | Hermida Ochoa |
| 2004/0214793 A1 | 10/2004 | Hermida Ochoa |
| 2004/0249463 A1 | 12/2004 | Bindseil et al. |
| 2005/0025809 A1 | 2/2005 | Hasirci et al. |
| 2005/0027033 A1* | 2/2005 | Knaack et al. ............... 523/115 |
| 2005/0142163 A1 | 6/2005 | Hunter et al. |
| 2005/0186261 A1 | 8/2005 | Avelar et al. |
| 2005/0197293 A1 | 9/2005 | Mellis et al. |
| 2006/0079773 A1 | 4/2006 | Mourad et al. |
| 2006/0106361 A1 | 5/2006 | Muni et al. |
| 2006/0148903 A1 | 7/2006 | Burch et al. |
| 2006/0189944 A1 | 8/2006 | Campbell et al. |
| 2006/0247772 A1 | 11/2006 | McKay |
| 2006/0270037 A1 | 11/2006 | Kato et al. |
| 2006/0293757 A1 | 12/2006 | McKay et al. |
| 2007/0077267 A1 | 4/2007 | Molz, IV et al. |
| 2007/0142916 A1 | 6/2007 | Olson, Jr. et al. |
| 2007/0156180 A1 | 7/2007 | Jaax et al. |
| 2007/0185367 A1 | 8/2007 | Abdou |
| 2007/0185497 A1 | 8/2007 | Cauthen et al. |
| 2007/0202074 A1 | 8/2007 | Shalaby |
| 2007/0243225 A1 | 10/2007 | McKay |
| 2007/0243228 A1 | 10/2007 | McKay |
| 2007/0259019 A1 | 11/2007 | McKay |
| 2008/0008988 A1 | 1/2008 | McKay et al. |
| 2008/0019969 A1 | 1/2008 | Gorman |
| 2008/0019970 A1 | 1/2008 | Gorman |
| 2008/0019975 A1 | 1/2008 | Gorman |
| 2008/0091207 A1 | 4/2008 | Truckai et al. |
| 2008/0147197 A1 | 6/2008 | McKay |
| 2008/0175911 A1 | 7/2008 | McKay et al. |
| 2008/0213283 A1 | 9/2008 | Olmarker et al. |
| 2008/0294261 A1 | 11/2008 | Pauza et al. |
| 2008/0317805 A1 | 12/2008 | McKay et al. |
| 2009/0024135 A1 | 1/2009 | Triplett et al. |

OTHER PUBLICATIONS

U.S. Appl. No. 12/397,405, filed Mar. 4, 2009.

* cited by examiner

RESORBABLE MATRIX HAVING ELONGATED PARTICLES

BACKGROUND

Bone is a composite material that is composed of impure hydroxyapatite, collagen and a variety of non-collagenous proteins, as well as embedded and adherent cells. Due to disease, a congenital defect or an accident, a person may lose or be missing part or all of one or more bones or regions of cartilage in his or her body, and/or have improper growth or formation of bone and/or cartilage.

Mammalian bone tissue is known to contain one or more proteinaceous materials that are active during growth and natural bone healing. These materials can induce a developmental cascade of cellular events that result in bone formation. Typically, the developmental cascade of bone formation involves chemotaxis of mesenchymal cells, proliferation of progenitor cells, differentiation of cartilage, vascular invasion, bone formation, remodeling and marrow differentiation.

When bone is damaged, often bone grafting procedures are performed to repair the damaged bone especially in cases where the damage is complex, poses a significant risk to the patient, and/or fails to heal properly. Bone grafting is also used to help fusion between vertebrae, correct deformities, or provide structural support for fractures of the spine. In addition to fracture repair, bone grafting is also used to repair defects in bone caused by birth defects, traumatic injury, or surgery for bone cancer.

There are at least three ways in which a bone graft can help repair a defect. The first is called osteogenesis, the formation of new bone within the graft. The second is osteoinduction, a process in which molecules contained within the graft (e.g., bone morphogenic proteins) convert the patient's cells into cells that are capable of forming bone. The third is osteoconduction, a physical effect by which a matrix often containing graft material acts as a scaffold on which bone and cells in the recipient are able to form new bone.

The source of bone for grafting can be obtained from bones in the patient's own body (e.g., hip, skull, ribs, etc.), called autograft, or from bone taken from other people that is frozen and stored in tissue banks, called allograft. The source of bone may also be derived from animals of a different species called a xenograft.

Some grafting procedures utilize a variety of natural and synthetic matrices with or instead of bone (e.g., collagen, silicone, acrylics, hydroxyapatite, calcium sulfate, ceramics, etc.). To place the matrix at the bone defect, the surgeon makes an incision in the skin over the bone defect and shapes the matrix to fit into the defect.

Often times, depending on the anatomic site for implantation, substantially spherical or rounded particles such as for example, bone particles, calcium phosphate ceramics, etc. are added to the matrix so that it can withstand certain loads that can be placed on it. They also enhance osseointegration of the matrix. While these particles added to the matrices provide some compression resistance, they often do not provide compression resistance in high load bearing areas such as for example in the spine. Therefore, as a result of excessive compression, the matrix may fail to integrate properly into the bone defect site or may be dislodge from the bone defect site to a blood vessel and cause an ischemic event (e.g., embolism, necrosis, edema, infarction, etc.), which could be detrimental to the patient.

As persons of ordinary skill are aware, growth factors (e.g., bone morphogenic protein-2) may be placed on the matrix in order to spur the patient's body to begin the formation of new bone and/or cartilage. These growth factors act much like a catalyst, encouraging the necessary cells (including, but not limited to, mesenchymal stem cells, osteoblasts, and osteoclasts) to more rapidly migrate into the matrix, which is eventually resorbed via a cell-mediated process and newly formed bone is deposited at or near the bone defect. In this manner severe fractures may be healed, and vertebrae successfully fused.

Sometimes when the surgeon manipulates the matrix to place it in the bone defect, excessive compression occurs causing increased amounts of growth factor (e.g., bone morphogenic protein) to leak from the matrix, which may reduce a stable microenvironment for new bone and/or cartilage growth. Thus, there is a need to develop new matrices that improve bone and/or cartilage repair.

SUMMARY

Compression resistant matrices are provided that improve stability and mechanical strength and resists shifting, extrusion and rotation after implantation. By using elongated particles in the matrix randomly or uniformly distributed throughout it, more compression resistance is achieved.

In some embodiments, the matrices provided reduce or prevent unwanted surface compression of the implantable matrix which will cause increased amounts of growth factor (e.g., bone morphogenic protein) to leak from the matrix.

In some embodiments, an implantable matrix is provided that is configured to fit at or near a target tissue site, the matrix comprising: a biodegradable polymer and a plurality of elongated particles embedded within the polymer, the elongated particles entangled with each other and embedded in the polymer uniformly or randomly so as to reduce compression of the matrix, wherein the matrix allows influx of at least progenitor, bone and/or cartilage cells therein.

In some embodiments, the matrix of the present application can reduce or prevent compression of the matrix from occurring during or after implantation. Compression of the matrix causes the growth factor to be forced into surrounding environment, which may lead to unwanted adverse events such as local transient bone resorption. Compression of the matrix can also cause buffer from the bone growth factor to leak from the matrix, which causes a higher concentration of the growth factor (e.g., rhBMP-2) to remain on the matrix. This high concentration of growth factor may lead to unwanted adverse events such as local transient bone resorption. By reducing compression of the matrix, leakage of the growth factor is prevented or reduced.

In some embodiments, by using a compression resistant matrix, the growth factor (e.g., rhBMP-2) will remain more evenly distributed throughout the matrix facilitating more uniform bone growth throughout the whole matrix.

In some embodiments, there is an implantable matrix configured to fit at or near a target tissue site, the matrix comprising: a biodegradable polymer and a plurality of elongated particles embedded within the polymer, the elongated particles embedded in the polymer uniformly or randomly so as to reduce compression of the matrix, wherein the matrix allows influx of at least progenitor, bone and/or cartilage cells therein.

In some embodiments, an implantable matrix configured to fit at or near a target tissue site is provided, the matrix comprising: collagen and a plurality of elongated mineral particles embedded within the collagen, the elongated mineral particles are entangled with each other and are embedded in the collagen uniformly or randomly so as to reduce compression of the matrix, wherein the matrix allows influx of at least progenitor, bone and/or cartilage cells therein; and the matrix comprises bone morphogenic protein.

In some embodiments, a method for making an implantable collagen matrix is provided, the method comprising: providing a quantity of elongated mineral particles, the elongated particles having a median length of from about 2 to about 20 mm, a median width of about 0.02 to about 5 mm and the ratio of median length to median width from about 10:1 to about 1000:1; and introducing them into a mold containing collagen, entangling the elongated mineral particles in the collagen uniformly or randomly to form the implant.

In some embodiments, there is a method of treating a bone defect in which the bone defect site possesses at least one cavity which comprises inserting a collagen matrix into the defect, the collagen matrix comprising a plurality of elongated ceramic particles embedded within the collagen, the elongated ceramic particles entangled with each other and embedded in the collagen uniformly or randomly so as to reduce compression of the matrix, wherein the matrix allows influx of at least progenitor, bone and/or cartilage cells therein; and the matrix comprises bone morphogenic protein.

In some embodiments, the implantable matrix will be useful in large oralmaxillofacial defects, building up alveolar and mandible ridge heights for future dental implant placement, cranial defects, long bone segmental defects, or posterolateral spine fusions.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1A:
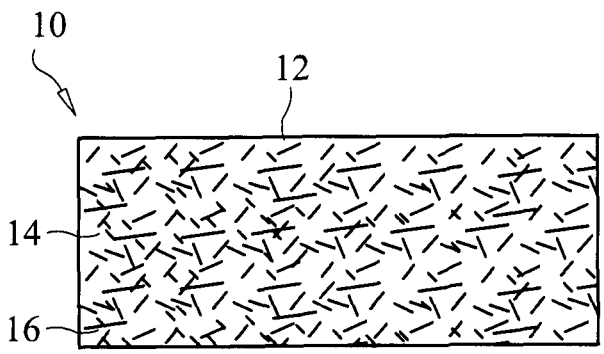
FIG. 1A illustrates a magnified side sectional view of an embodiment of the implantable matrix shown having elongated particles shown as fibers embedded randomly throughout it. The implantable matrix is shown in an uncompressed state.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations; the numerical values are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this invention belongs.

Unless explicitly stated or apparent from context, the following terms or phrases have the definitions provided below:
Definitions It is noted that, as used in this specification and the appended claims, the singular forms "a," "an," and "the," include plural referents unless expressly and unequivocally limited to one referent. Thus, for example, reference to "a matrix" includes one, two, three or more matrices.

The term "biodegradable" includes that all or parts of the matrix will degrade over time by the action of enzymes, by hydrolytic action and/or by other similar mechanisms in the human body. In various embodiments, "biodegradable" includes that a matrix (e.g., sponge, sheet, etc.) can break down or degrade within the body to non-toxic components after or while a therapeutic agent has been or is being released. By "bioerodible" it is meant that the matrix will erode or degrade over time due, at least in part, to contact with substances found in the surrounding tissue, fluids or by cellular action. By "bioabsorbable" or "bioresorbable" it is meant that the matrix will be broken down and absorbed within the human body, for example, by a cell or tissue. "Biocompatible" means that the matrix will not cause substantial tissue irritation or necrosis at the target tissue site.

The term "mammal" refers to organisms from the taxonomy class "mammalian," including but not limited to humans, other primates such as chimpanzees, apes, orangutans and monkeys, rats, mice, cats, dogs, cows, horses, etc.

The term "resorbable" includes biologic elimination of the products of degradation by metabolism and/or excretion over time, for example, usually months.

The term "particle" refers to pieces of a substance of all shapes, sizes, thickness and configuration such as fibers, threads, narrow strips, thin sheets, clips, shards, etc., that posses regular, irregular or random geometries. In some embodiments, the particles are elongated having more length than width (e.g., long and slender particles). It should be understood that some variation in dimension will occur in the production of the particles and particles demonstrating such variability in dimensions are within the scope of the present application.

The term "target tissue site" is intended to mean the location of the tissue to be treated. Typically the placement site of the matrix will be the same as the target site to provide for optimal targeted drug delivery. However, the present application also contemplates positioning the matrix at a placement site at or near the target site such that the therapeutic agent (e.g., growth factor) can be delivered to the surrounding vasculature, which carries the agent to the desired nearby target site. As used herein, the term "at or near" includes embodiments where the placement site and target site are within close proximity (e.g., within about 1 mm to 5 cm).

The term "autograft" as utilized herein refers to tissue that is extracted from the intended recipient of the implant. These include elongated particles.

The term "allograft" as utilized herein refers to tissue intended for implantation that is taken from a different member of the same species as the intended recipient. These include elongated particles.

The term "xenogenic" as utilized herein refers to material intended for implantation obtained from a donor source of a different species than the intended recipient. For example, when the implant is intended for use in an animal such as a horse (equine), xenogenic tissue of, e.g., bovine, porcine, caprine, etc., origin may be suitable. These include elongated particles.

The term "transgenic" as utilized herein refers to tissue intended for implantation that is obtained from an organism that has been genetically modified to contain within its genome certain genetic sequences obtained from the genome of a different species. The different species is usually the same species as the intended implant recipient but such limitation is merely included by way of example and is not intended to limit the disclosure here in anyway whatsoever. These include elongated particles.

The expressions "whole bone" and "substantially fully mineralized bone" refer to bone containing its full or substantially full, original mineral content that can be used. This type of bone can be used to make elongated particles.

The expression "demineralized bone" includes bone that has been partially, fully, segmentally or superficially (surface) demineralized. This type of bone can be used to make elongated particles.

The expression "substantially fully demineralized bone" as utilized herein refers to bone containing less than about 8% of its original mineral context. This type of bone can be used to make elongated particles.

A "therapeutically effective amount" or "effective amount" is such that when administered, the drug (e.g., growth factor) results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the implantable matrix is designed for sustained release. In some embodiments, the implantable matrix comprises an effective amount of a growth factor.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug.

The phrases "prolonged release", "sustained release" or "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the matrix and/or component thereof, or as the result of metabolic transformation or dissolution of the therapeutic agent(s) or conjugates of therapeutic agent(s). The release need not be linear and can be pulse type dosing.

The "matrix" of the present application is utilized as a scaffold for bone and/or cartilage repair, regeneration, and/or augmentation. Typically, the matrix provides a 3-D matrix of interconnecting pores, which acts as a pliant scaffold for cell migration. The morphology of the matrix guides cell migration and cells are able to migrate into or over the matrix, respectively. The cells then are able to proliferate and synthesize new tissue and form bone and/or cartilage. In some embodiments, the matrix is resorbable.

In some embodiments, the matrix can be shaped. The term "shaped" includes that the matrix including the elongated particles is formed into sheets, plates, disks, cones, pins, screws, tubes, teeth, bones, portion of bone, wedges, cylinders, threaded cylinders, and the like, as well as more complex geometric configurations.

The term "aggregate" as applied to the aggregate of elongated particles refers to that the particles adhere to each other where they clump to each other in a mass, e.g., by use of a biocompatible binder or adhesive. In some embodiments, the elongated particles do not aggregate where they contact each other by overlapping with each other but remain separate (e.g., tether each other).

The term "compression" refers to a reduction in size or an increase in density when a force is applied to the matrix.

The terms "treating" and "treatment" when used in connection with a disease or condition refer to executing a protocol that may include a repair procedure (e.g., osteochondral repair procedure), administering one or more matrices to a patient (human or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient. In some embodiments, the implantable matrix can be used to treat subchondral, osteochondral, hyaline cartilage and/or condyle defects.

The term "subchondral" includes an area underlying joint cartilage. The term "subchondral bone" includes a very dense, but thin layer of bone just below a zone of cartilage and above the cancellous or trabecular bone that forms the bulk of the bone structure of the limb. "Osteochondral" includes a combined area of cartilage and bone where a lesion or lesions can occur. "Osteochondral defect" includes a lesion, which is a composite lesion of cartilage and subchondral bone. "Hyaline cartilage" includes cartilage containing groups of isogenous chondrocytes located within lacunae cavities which are scattered throughout an extracellular collagen matrix. A "condyle" includes a rounded articular surface of the extremity of a bone.

The matrix may be osteogenic. The term "osteogenic" as used herein includes the ability of the matrix to enhance or accelerate the growth of new bone tissue by one or more mechanisms such as osteogenesis, osteoconduction and or osteoinduction. In some embodiments, the matrix is osteogenic and can be delivered to other surgical sites, particularly sites at which bone growth is desired. These include, for instance, the repair of spine (e.g., vertebrae fusion) cranial defects, iliac crest back-filling, acetabular defects, in the repair of tibial plateau, long bone defects, spinal site defects or the like. Such methods can be used to treat major or minor defects in these or other bones caused by trauma (including open and closed fractures), disease, or congenital defects, for example.

The matrix may be osteoinductive. The term "osteoinductive" as used herein includes the ability of a substance to recruit cells from the host that have the potential for forming new bone and repairing bone tissue. Most osteoinductive materials can stimulate the formation of ectopic bone in soft tissue.

The matrix may be osteoconductive. The term "osteoconductive" as utilized herein includes the ability of a non-osteoinductive substance to serve as a suitable template or substrate along which bone may grow.

The matrix may be implantable. The term "implantable" as utilized herein refers to a biocompatible device retaining potential for successful placement within a mammal. The expression "implantable device" and expressions of like import as utilized herein refers to any object implantable through surgery, injection, or other suitable means whose primary function is achieved either through its physical presence or mechanical properties.

The term "carrier" includes a diluent, adjuvant, buffer, excipient, or vehicle with which a composition can be administered. Carriers can include sterile liquids, such as, for example, water and oils, including oils of petroleum, animal, vegetable or synthetic origin, such as, for example, peanut oil, soybean oil, mineral oil, sesame oil, or the like. The growth factor may include a carrier.

The term "excipient" includes a non-therapeutic agent added to a pharmaceutical composition to provide a desired consistency or stabilizing effect. Excipients for parenteral formulations, include, for example, oils (e.g., canola, cottonseed, peanut, safflower, sesame, soybean), fatty acids and salts and esters thereof (e.g., oleic acid, stearic acid, palmitic acid), alcohols (e.g., ethanol, benzyl alcohol), polyalcohols (e.g., glycerol, propylene glycols and polyethylene glycols, e.g., PEG 3350), polysorbates (e.g., polysorbate 20, polysorbate 80), gelatin, albumin (e.g., human serum albumin), salts (e.g., sodium chloride), succinic acid and salts thereof (e.g., sodium succinate), amino acids and salts thereof (e.g., alanine, histidine, glycine, arginine, lysine), acetic acid or a salt or ester thereof (e.g., sodium acetate, ammonium acetate), citric acid and salts thereof (e.g., sodium citrate), benzoic acid and salts thereof, phosphoric acid and salts thereof (e.g., monobasic sodium phosphate, dibasic sodium phosphate), lactic acid and salts thereof, polylactic acid, glutamic acid and salts thereof (e.g., sodium glutamate), calcium and salts thereof (e.g., $CaCl_2$, calcium acetate), phenol, sugars (e.g., glucose, sucrose, lactose, maltose, trehalose), erythritol, arabitol, isomalt, lactitol, maltitol, mannitol, sorbitol, xylitol, nonionic surfactants (e.g., TWEEN 20, TWEEN 80), ionic surfactants (e.g., sodium dodecyl sulfate), chlorobutanol, DMSO, sodium hydroxide, glycerin, m-cresol, imidazole, protamine, zinc and salts thereof (e.g, zinc sulfate), thimerosal, methylparaben, propylparaben, carboxymethylcellulose, chlorobutanol, or heparin. The growth factor may include an excipient.

The term "lyophilized" or "freeze-dried" includes a state of a substance that has been subjected to a drying procedure such as lyophilization, where at least 50% of moisture has been removed. The matrix and/or growth factor may be lyophilized or freeze-dried.

A "preservative" includes a bacteriostatic, bacteriocidal, fungistatic or fungicidal compound that is generally added to formulations to retard or eliminate growth of bacteria or other contaminating microorganisms in the formulations. Preservatives include, for example, benzyl alcohol, phenol, benzalkonium chloride, m-cresol, thimerosol, chlorobutanol, methylparaben, propylparaben and the like. Other examples of pharmaceutically acceptable preservatives can be found in the USP. The growth factor and/or matrix may have preservatives or be preservative free.

Reference will now be made in detail to certain embodiments of the invention. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Compression resistant matrices are provided that improve stability and mechanical strength and resists shifting, extrusion and rotation after implantation. By using elongated particles in the matrix randomly or uniformly distributed throughout it, more compression resistance is achieved. This is particularly so when compared to conventional matrices that contain only substantially spherical or rounded particles.

In some embodiments, an implantable matrix is provided that is configured to fit at or near a target tissue site, the matrix comprising: a biodegradable polymer and a plurality of elongated particles embedded within the polymer, the elongated particles entangled with each other and embedded in the polymer uniformly or randomly so as to reduce compression of the matrix, wherein the matrix allows influx of at least progenitor, bone and/or cartilage cells therein.

In some embodiments, the matrix of the present application can reduce or prevent compression of the implantable matrix from occurring. Often compression of the implantable matrix causes the growth factor to be forced into surrounding environment, which may lead to unwanted adverse events such as local transient bone resorption. Compression of the matrix can also cause buffer from the bone growth factor to leak from the matrix, which causes a higher concentration of the growth factor (e.g., rhBMP-2) to remain on the matrix. This high concentration of growth factor may lead to local transient bone resorption as well. By employing elongated bone particles in the interior matrix compression is reduced and thus leakage of the growth factor and/or buffer is prevented and/or reduced.

It will be understood by those of ordinary skill in the art that in some embodiments, some compression may occur during implantation when the matrix is manipulated into the target tissue, which may cause release the growth factor (e.g., less than 0.75 M Pa, or 0.5 M Pa, or 0.25 M Pa of pressure), which may release less than 5%, 4%, 3%, 2%, 1%, or 0.5% w/w or w/v of the growth factor. But the release will be minimal or non-existent because the elongated particles in the matrix reduce or prevent compression.

In some embodiments, the growth factor (e.g., rhBMP-2) will be more evenly distributed throughout the interior of the matrix and facilitate more uniform bone growth throughout the whole matrix. In some embodiments, the growth factor (e.g., rhBMP-2) is temporarily retained within the matrix so as to limit new bone formation to within the matrix.

By reducing compression, the matrix of the present application allows the growth factor to stay evenly distributed within the interior of the matrix and thus avoids uneven distribution of the growth factor, for example, where a low dose of growth factor is distributed in the upper portion of the matrix, which may promote cartilage or soft tissue formation at the target tissue site.

The headings below are not meant to limit the disclosure in any way; embodiments under any one heading may be used in conjunction with embodiments under any other heading.

Matrix

The matrix provides a tissue scaffold for the cells to guide the process of tissue formation in vivo in three dimensions. The morphology of the matrix guides cell migration and cells are able to migrate into or over the matrix. The cells then are able to proliferate and synthesize new tissue and form bone and/or cartilage. In some embodiments, one or more tissue matrices are stacked on one another.

The matrix is porous and configured to allow influx of at least bone and/or cartilage cells therein. In some embodiments, the matrix is also configured to release a growth factor. By porous is meant that the matrix has a plurality of pores. The pores of the matrix are a size large enough to allow influx of blood, other bodily fluid, and progenitor and/or bone and/or cartilage cells into the interior to guide the process of tissue formation in vivo in three dimensions.

In some embodiments, the matrix comprises a plurality of pores. In some embodiments, at least 10% of the pores are between about 50 micrometers and about 500 micrometers at their widest points. In some embodiments, at least 20% of the pores are between about 50 micrometers and about 250 micrometers at their widest points. In some embodiments, at least 30% of the pores are between about 50 micrometers and about 150 micrometers at their widest points. In some embodiments, at least 50% of the pores are between about 10 micrometers and about 500 micrometers at their widest points. In some embodiments, at least 90% of the pores are between about 50 micrometers and about 250 micrometers at their widest points. In some embodiments, at least 95% of the pores are between about 50 micrometers and about 150 micrometers at their widest points. In some embodiments, 100% of the pores are between about 10 micrometers and about 500 micrometers at their widest points.

In some embodiments, the matrix has a porosity of at least about 30%, at least about 50%, at least about 60%, at least about 70%, at least about 90% or at least about 95%, or at least about 99%. The pores may support ingrowth of cells, formation or remodeling of bone, cartilage and/or vascular tissue.

In some embodiments, the matrix does not contain any growth factor. In some embodiments, the matrix does contain one or more growth factors.

In some embodiments, the porous interior can hold the growth factor within the matrix and because the interior is porous, the growth factor is evenly distributed throughout the matrix when growth factor is injected into the matrix.

In some embodiments, growth factor will be held within the interior of the matrix and released into the environment surrounding the matrix (e.g., bone defect, osteochondral defect, etc.) as the matrix degrades over time In some embodiments, the matrix comprises biodegradable polymeric and non-polymeric material. For example, the matrix may comprises one or more poly (alpha-hydroxy acids), poly (lactide-co-glycolide) (PLGA), polylactide (PLA), poly(L-lactide), polyglycolide (PG), polyethylene glycol (PEG) conjugates of poly (alpha-hydroxy acids), poly-orthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherketone, polymethylmethacrylate, silicone, hyaluronic acid, chitosan, or combinations thereof.

Because the matrix has elongated particles uniformly or randomly distributed throughout it, the matrix is substantially rigid and resists compression. For example, in some embodiments, the matrix may have a modulus of elasticity between 1.0 MPa and 20.0 MPa, or 2.0 MPa and 10.0 MPa or between 3.0 MPa and 5.0 MPa, with the higher MPa values obtainable by cross-linking.

In some embodiments, the matrix (e.g., exterior and/or interior) comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the matrix comprises collagen-containing biomaterials from the implant market which, when placed in a bone defect, provide scaffolding around which the patient's new bone and/or cartilage will grow, gradually replacing the carrier matrix as the target site heals. Examples of suitable carrier matrices may include, but are not limited to, the MasterGraft® Matrix produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g. Healos®. marketed by Johnson & Johnson, USA; collagen sponges, e.g. Hemostagene® marketed by Coletica S A, France, or e.g. Helisat® marketed by Integra Life Sciences Inc., USA; and Collagraft® Bone Graft Matrix produced by Zimmer Holdings, Inc., Warsaw, Ind.

Compression resistance is needed for many tissue engineering applications such as tibial plateau fractures, acetabular defects, long bone comminuted fractures, oral maxillofacial defects, spinal fusions, and cartilage subchondral defects. Compression resistant matrices will help facilitate adequate volumes of newly formed bone.

In some embodiments, the matrix is compression resistant where the matrix resists reduction in size or an increase in density when a force is applied as compared to matrices without the elongated particles disposed in it. In various embodiments, the matrix resists compression by at 10%, 15%, 20%, 25%, 30%, 35%, 40%, 45%, 50%, 55%, 60%, 65%, 70%, 75%, 80%, 85%, 90%, 95%, or more in one or all directions when a force is applied to the matrix.

Elongated Particles

The matrix comprises elongated particles. The elongated particles offer better compression resistance because of the increased interaction of the elongated particles than conventional rounded or spherical particles. When elongated particles are embedded in a polymer matrix, the elongated particles are tethered along their length therefore resisting movement when compressed.

In some embodiments, the elongated particles comprise at least 10%, 15%, 20%, 25%, 30%, 35%, 40%, 45%, 50%, 55%, 60%, 65%, 70%, 75%, 80%, 85%, 90%, 95% by weight of the matrix. In some embodiments, the particles are predominantly elongated (powders, chips, fibers, cylinders, etc.). In some embodiments, there are non-elongated particles (e.g., rounded or spherical) in the matrix, but this does not make up a predominant amount of the particle type. In some embodiments, the particles in the matrix consist solely of elongated particles.

In some embodiments, the particles (bone and non-bone particles) are elongated i.e., they possess relatively high median length to median thickness ratios. In overall appearance, the elongate particles can be described as filaments, fibers, threads, slender or narrow strips, etc. Thus, e.g., the elongate particles can possess a median length of from about 2 to about 20 mm, or a median width of from about 0.02 to about 5 mm or the ratio of median length to median width is from about 10:1 to about 1000:1. In some embodiments, the elongated particles have a median length of from about 1 to about 10 mm, the median width of the elongated particles is from about 0.04 to about 2 mm and the ratio of median length to median width is from about 20:1 to about 200:1.

If desired, the elongate particles can be graded into different sizes to reduce or eliminate any less desirable size(s) of particles that may be present.

In some embodiments, the porosity of the elongated particles comprises from 0 to 50%, in some embodiments, the porosity of the elongated particles comprises 5% to 25%.

In some embodiments, the elongated particles are not entangled with each other but contact each other and portions of each elongated particle overlap in the matrix to provide compression resistance. In some embodiments, at least 50%, 55%, 60%, 65%, 70%, 75%, 80%, 85%, 90%, 95%, or more of the elongated particles overlap each other in the matrix.

In some embodiments, the elongated particles are not aggregated (e.g., they do not clump together in a mass) in the matrix.

In some embodiments, the elongated particles are randomly distributed throughout the matrix. In other embodiments, the elongated particles are uniformly or evenly distributed throughout the matrix. In some embodiments, the elongated particles may be dispersed in the matrix using a dispersing agent. In other embodiments, the elongated particles may be stirred in the polymer and the mechanical agitation will distribute the particles in the matrix until the desired distribution is reached (e.g., random or uniform)

The elongate particles can be readily obtained by any one of several methods, e.g., by milling or shaving the surface of an entire bone or relatively large section of bone. Employing a milling technique, one can obtain a mass of elongate particles containing at least about 20 weight percent of particles coming within the aforesaid range of dimensions.

In some embodiments, the matrix may comprise a resorbable ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof.

In some embodiments, the matrix may be seeded with harvested bone cells and/or bone tissue, such as for example, cortical bone, autogenous bone, allogenic bones and/or xenogenic bone. In some embodiments, the matrix may be seeded with harvested cartilage cells and/or cartilage tissue (e.g., autogenous, allogenic, and/or xenogenic cartilage tissue). For example, before insertion into the target tissue site, the matrix can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the matrix provided, and the matrix may be kneaded by hand or machine, thereby obtaining a pliable consistency that may subsequently be packed into the bone defect. In some embodiments, the matrix provides a malleable, non-water soluble carrier that permits accurate placement and retention at the implantation site. In some embodiments, the harvested bone and/or cartilage cells can be mixed with the growth factor and seeded in the interior of the matrix.

In some embodiments, the elongated particles in the matrix comprise a resorbable ceramic, bone, synthetic degradable polymer, hyaluronic acid, chitosan or combinations thereof. In some embodiments, the elongated particles comprise cortical, cancellous, and/or corticocancellous, allogenic, xenogenic or transgenic bone tissue. The bone component can be fully mineralized or partially or fully demineralized or combinations thereof. The bone component can consist of fully mineralized or partially or fully demineralized bone.

In some embodiments, the matrix may contain an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, by including inorganic ceramics, such as for example, calcium phosphate, in the matrix, this will facilitate the prevention of local bone resorption by providing slower release of the growth factor due to its increased binding potential and also act as a local source of calcium and phosphate to the cells attempting to deposit new bone. The inorganic ceramic also provides compression resistance and load bearing characteristics to the matrix.

In some embodiments, the elongated particles in the matrix comprise tricalcium phosphate and hydroxyapatite in a ratio of about 80:20 to about 90:10. In some embodiments, the elongated particles in the matrix comprise tricalcium phosphate and hydroxyapatite in a ratio of about 85:15.

In some embodiments, tissue will infiltrate the matrix to a degree of about at least 50 percent within about 1 month to about 6 months after implantation of the matrix. In some embodiments, about 75 percent of the matrix will be infiltrated by tissue within about 2-3 months after implantation of the matrix. In some embodiments, the matrix will be substantially, e.g., about 90 percent or more, submerged in or enveloped by tissue within about 6 months after implantation of the matrix. In some embodiments, the matrix will be completely submerged in or enveloped by tissue within about 9-12 months after implantation.

In some embodiments, the matrix has a thickness of from 1 mm to 15 mm, or from about 2 mm to about 10 mm, or 3 mm to about 5 mm. Clearly, different bone defects (e.g., osteochondral defects) may require different matrices thicknesses.

In some embodiments, the matrix has a density of between about 1.6 g/cm$^3$, and about 0.05 g/cm$^3$. In some embodiments, the matrix has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

The shape of the matrix may be tailored to the site at which it is to be situated. For example, it may be in the shape of a morsel, a plug, a pin, a peg, a cylinder, a block, a wedge, a sheet, a strip, etc. The term "shape" refers to a determined or regular form or configuration in contrast to an indeterminate or vague form or configuration (as in the case of a lump or other solid mass of no special form) and is characteristic of such materials as sheets, plates, disks, cores, tubes, wedges, cylinders, or the like. This includes forms ranging from regular, geometric shapes to irregular, angled, or non-geometric shapes, or combinations of features having any of these characteristics.

In some embodiments, the diameter or diagonal of the matrix can range from 1 mm to 50 mm. In some embodiments, the diameter or diagonal of the matrix can range from 1 mm to 30 mm, or 5 mm to 10 mm which is small enough to fit through an endoscopic cannula, but large enough to minimize the number of matrices needed to fill a large the bone defect (e.g., osteochondral defect). In some embodiments, at the time of surgery, the matrix can be cut by the surgeon to the desired shape to fit the tissue or bone defect and possibly hydrated with a growth factor if necessary.

FIG. 1A illustrates a magnified side sectional view of an embodiment of the implantable matrix 10 shown having elongated particles 16 shown as fibers embedded randomly throughout it. The elongated particles 16 overlap with each other and are entangled in the matrix. These elongated particles act like tethers and provide compression resistance to the entire matrix. In this figure, the implantable matrix is shown in an uncompressed state as the surface 12 retains its shape. The matrix is porous and the pores are shown as 14 in between the elongated particles. The pores will allow cell migration into or over the porous interior of the matrix to enhance bone and/or cartilage remodeling. The pores also allow the introduction of the growth factor as well.

Figure 1B:
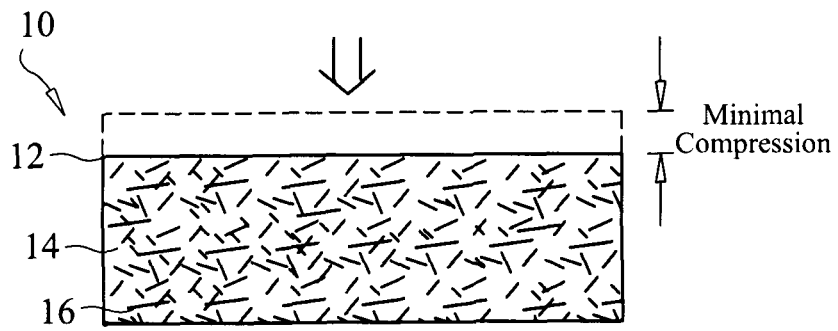
FIG. 1B illustrates a magnified side sectional view of an embodiment of the implantable matrix shown having elongated particles shown as fibers embedded randomly throughout it. The implantable matrix is shown having minimal compression.

FIG. 1B illustrates a magnified side sectional view of an embodiment of the implantable matrix 10 shown having elongated particles 16 shown as fibers embedded randomly throughout it. The elongated particles 16 overlap with each other in the matrix. These elongated particles act like tethers and provide compression resistance. Once a load bearing force is applied to the matrix. The matrix is compressed minimally (e.g., less than 10%) as indicated by the arrow and the broken line and the surface 12. The surface 12 retains substantially all its shape in response to the load bearing event. It will be understood that the load bearing event can be applied to the matrix at any and all direction (e.g., right, left, up, down, back, front). In this figure, the matrix is porous and the pores are shown as 14 in between the elongated particles. The pores will allow cell migration into or over the porous interior of the matrix to enhance bone and/or cartilage remodeling. The pores also allow the introduction of the growth factor as well.

Figure 2A:
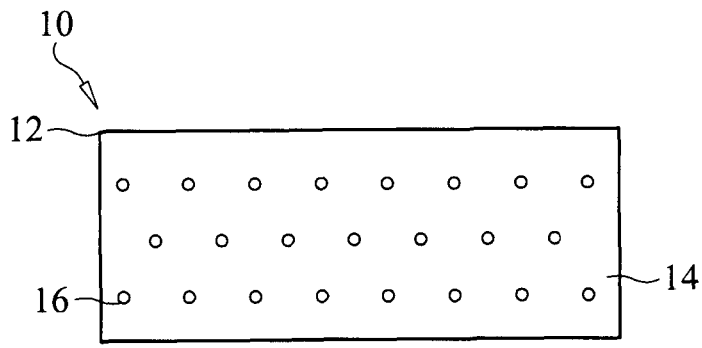
FIG. 2A illustrates a magnified side sectional view of a commercially available collagen sponge having rounded particles disposed uniformly in the matrix. In this illustrated embodiment, the collagen sponge is shown in an uncompressed state.
Figure 2B:
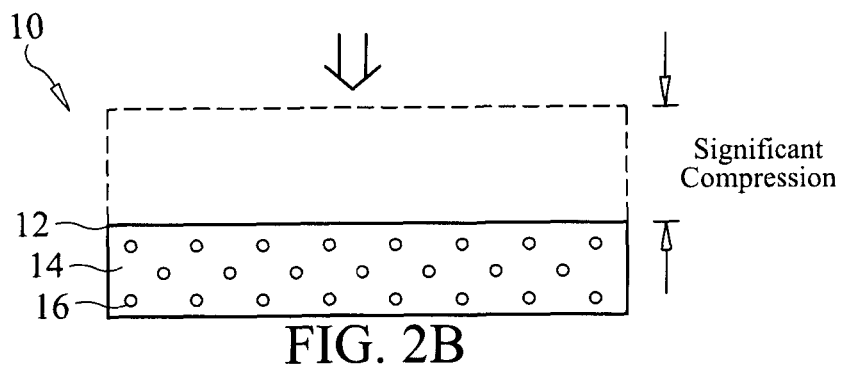
FIG. 2B illustrates a magnified side sectional view of a commercially available collagen sponge having rounded particles disposed uniformly in the matrix. In this illustrated embodiment, the collagen sponge is shown having significant compression (e.g., at least 50% in thickness).

Conventional matrices are shown in FIG. 2A, which illustrates a magnified side sectional view of a commercially available collagen sponge 10 having rounded particles 16 disposed uniformly in the matrix. In this illustrated embodiment, the collagen sponge is shown in an uncompressed state 12 and has pores 14. This type of conventional collagen sponge does not resist compression. FIG. 2B illustrates a magnified side sectional view of a commercially available collagen sponge 10 having rounded particles 16 and pores 14 disposed uniformly in the matrix. In this illustrated embodiment, the collagen sponge is shown having significant compression 12 (e.g., at least 50% of the sponge is compressed when a load bearing event occurs, as indicated by the broken lines).

Figure 3:
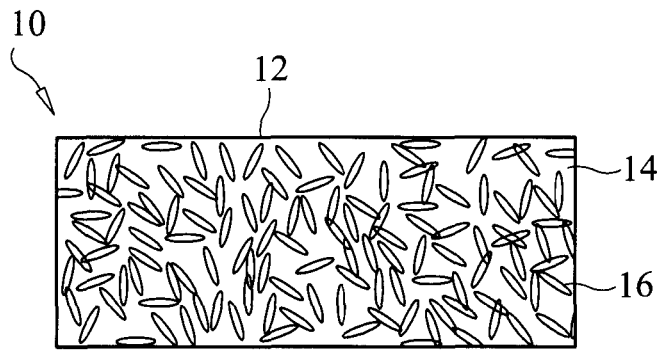
FIGS. 3-4 illustrate magnified side sectional views of different embodiments of the implantable matrix shown having different shaped elongated particles embedded randomly throughout it. The implantable matrix is shown in an uncompressed state.
Figure 4:
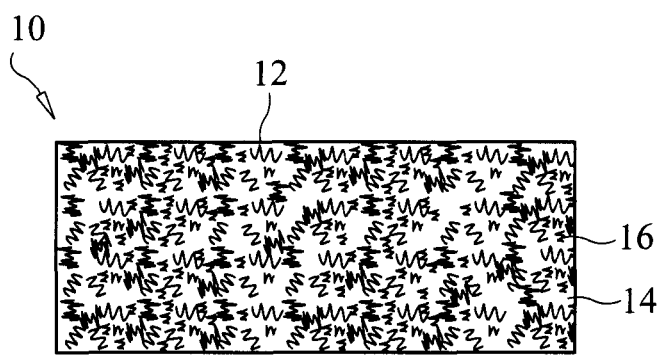

FIGS. 3-4 illustrate magnified side sectional views of different embodiments of the implantable matrix 10 shown having elongated particles 16 shown as fibers embedded randomly throughout it. The elongated particles 16 overlap with each other and are entangled in the matrix. These elongated particles act like tethers and provide compression resistance. The implantable matrix is shown in an uncompressed state as the surface 12 retains its shape. The matrix is porous and the pores are shown as 14 in between the elongated particles. The pores will allow cell migration into or over the porous interior of the matrix to enhance bone and/or cartilage remodeling. The pores also allow the introduction of the growth factor as well.

Figure 5:
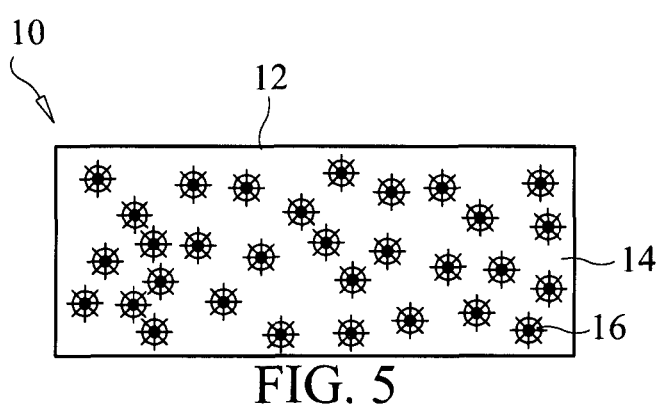
FIGS. 5-6 illustrate magnified side sectional views of different embodiments of the implantable matrix shown having different shaped elongated particles embedded more uniformly throughout it. The implantable matrix is shown in an uncompressed state.
Figure 6:
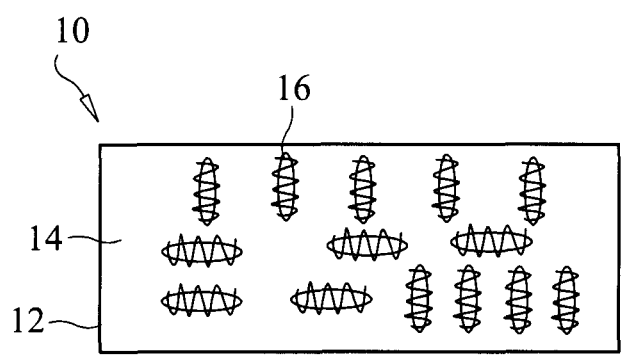

FIGS. 5-6 illustrate magnified side sectional views of different embodiments of the implantable matrix 10 shown having elongated particles 16 shown as cancellous bone chips or synthetic calcium phosphate chips (FIG. 5) and elongated shapes (FIG. 6) embedded uniformly throughout the matrix. The elongated particles 16 overlap with each other and are entangled in the matrix. These elongated particles act like tethers and provide compression resistance. The implantable matrix is shown in an uncompressed state as the surface 12 retains its shape. The matrix is porous and the pores are shown as 14 in between the elongated particles. The pores will allow cell migration into or over the porous interior of the matrix to enhance bone and/or cartilage remodeling. The pores also allow the introduction of the growth factor as well.

Although the matrix is shown as a sponge in the figures, it will be understood by one of ordinary skill in the art that the matrix can be made of other material in different shapes and sizes depending on the condition being treated.

Method of Making Matrix

In some embodiments, the matrix may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

One form of manufacturing the matrix involves casting the matrix material in a mold. The matrix material can take on the shape of the mold such as, crescent, quadrilateral, rectangular, cylindrical, plug, or any other shape. Additionally, the surface of the mold may be smooth or may include raised features or indentations to impart features to the matrix. Features from the mold can be imparted to the matrix as the matrix material in the mold is dried. In particular aspects, a roughened or friction engaging surface can be formed on the superior surface and/or the inferior surface of the matrix body. In some embodiments, protuberances or raised portions can be imparted on the superior surface and/or the inferior surface from the mold. Such examples of protuberances or raised portions are ridges, serrations, pyramids, and teeth, or the like.

In some embodiments, in manufacturing the matrix, a mixture of the matrix material (e.g., collagen) is combined with the elongated particles and a liquid to wet the material and form a slurry. Any suitable liquid can be used including, for example, aqueous preparations such as water, saline solution (e.g. physiological saline), sugar solutions, protic organic solvents, or liquid polyhydroxy compounds such as glycerol and glycerol esters, or mixtures thereof. The liquid may, for example, constitute about 5 to about 70 weight percent of the mixed composition prior to the molding operation. Certain liquids such as water can be removed in part or essentially completely from the formed matrix using conventional drying techniques such as air drying, heated drying, lyophilization, or the like.

In one embodiment of manufacture, a collagen mixture can be combined with a elongated particles and a liquid, desirably with an aqueous preparation, to form a slurry. Excess liquid can be removed from the slurry by any suitable means, including for example by applying the slurry to a liquid-permeable mold or form and draining away excess liquid.

Before, during or after molding, including in some instances the application of compressive force to the collagen containing material, the collagen material can be subjected to one or more additional operations such as heating, lyophilizing and/or crosslinking to make the porous collagen interior or exterior of the matrix the desired porosity. In this regard, crosslinking can be used to improve the strength of the formed matrix. Alternatively, one or more of the surface of the matrix can be crosslinked to reduce the size of the pores of the porous interior and thereby form the exterior of the matrix that is less permeable and/or less porous than the porous interior. Crosslinking can be achieved, for example, by chemical reaction, the application of energy such as radiant energy (e.g. UV light or microwave energy), drying and/or heating and dye-mediated photo-oxidation; dehydrothermal treatment; enzymatic treatment or others.

Chemical crosslinking agents will generally be preferred, including those that contain bifunctional or multifunctional reactive groups, and which react with matrix. Chemical crosslinking can be introduced by exposing the matrix material to a chemical crosslinking agent, either by contacting it with a solution of the chemical crosslinking agent or by exposure to the vapors of the chemical crosslinking agent. This contacting or exposure can occur before, during or after a molding operation. In any event, the resulting material can then be washed to remove substantially all remaining amounts of the chemical crosslinker if needed or desired for the performance or acceptability of the final implantable matrix.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante; and/or sugars, including glucose, will also crosslink the matrix material.

In some embodiments, the matrices are formed by mixing the elongated particles in with a polymer slurry such as collagen and pouring into a shaped mold. The composite mixture is freeze dried and possibly chemically crosslinked and cut to the final desired shape.

In some embodiments, an implantable matrix is provided that is configured to fit at or near a target tissue site, the matrix comprising: collagen and a plurality of elongated mineral particles embedded within the collagen, the elongated mineral particles being entangled with each other and embedded in the collagen uniformly or randomly so as to reduce compression of the matrix, wherein the matrix allows influx of at least progenitor, bone and/or cartilage cells therein; and the matrix comprises bone morphogenic protein.

In some embodiments, the matrix may comprise sterile and/or preservative free material. The matrix can be implanted by hand or machine in procedures such as for example, laparoscopic, arthroscopic, neuroendoscopic, endoscopic, rectoscopic procedures or the like.

The matrix of the present application may be used to repair bone and/or cartilage at a target tissue site, e.g., one resulting from injury, defect brought about during the course of surgery, infection, malignancy or developmental malformation. The matrix can be utilized in a wide variety of orthopedic, periodontal, neurosurgical, oral and maxillofacial surgical procedures such as the repair of simple and/or compound fractures and/or non-unions; external and/or internal fixations; joint reconstructions such as arthrodesis; general arthroplasty; cup arthroplasty of the hip; femoral and humeral head replacement; femoral head surface replacement and/or total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay implantable matrices; implant placement and revision; sinus lifts; cosmetic procedures; etc. Specific bones which can be repaired or replaced with the implantable matrix herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and/or metatarsal bones.

Growth Factors

In some embodiments, a growth factor and/or therapeutic agent may be disposed on or in the matrix by hand, electrospraying, ionization spraying or impregnating, vibratory dispersion (including sonication), nozzle spraying, compressed-air-assisted spraying, injecting, brushing and/or pouring. For example, a growth factor such as rhBMP-2 may be disposed on or in the biodegradable matrix by the surgeon before the biodegradable matrix is administered or the matrix may be pre-loaded with the growth factor by the manufacturer beforehand.

The biodegradable matrix may comprise at least one growth factor. These growth factors include osteoinductive agents (e.g., agents that cause new bone growth in an area where there was none) and/or osteoconductive agents (e.g., agents that cause ingrowth of cells into and/or through the matrix). Osteoinductive agents can be polypeptides or polynucleotides compositions. Polynucleotide compositions of the osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta) polynucleotides. Polynucleotide compositions of the osteoinductive agents include, but are not limited to, gene therapy vectors harboring polynucleotides encoding the osteoinductive polypeptide of interest. Gene therapy methods often utilize a polynucleotide, which codes for the osteoinductive polypeptide operatively linked or associated to a promoter or any other genetic elements necessary for the expression of the osteoinductive polypeptide by the target tissue. Such gene therapy and delivery techniques are known in the art (see, for example, International Publication No. WO90/11092, the disclosure of which is herein incorporated by reference in its entirety). Suitable gene therapy vectors include, but are not limited to, gene therapy vectors that do not integrate into the host genome. Alternatively, suitable gene therapy vectors include, but are not limited to, gene therapy vectors that integrate into the host genome.

In some embodiments, the polynucleotide is delivered in plasmid formulations. Plasmid DNA or RNA formulations refer to polynucleotide sequences encoding osteoinductive polypeptides that are free from any delivery vehicle that acts to assist, promote or facilitate entry into the cell, including viral sequences, viral particles, liposome formulations, lipofectin, precipitating agents or the like. Optionally, gene therapy compositions can be delivered in liposome formulations and lipofectin formulations, which can be prepared by methods well known to those skilled in the art. General methods are described, for example, in U.S. Pat. Nos. 5,593,972, 5,589,466, and 5,580,859, the disclosures of which are herein incorporated by reference in their entireties.

Gene therapy vectors further comprise suitable adenoviral vectors including, but not limited to for example, those described in U.S. Pat. No. 5,652,224, which is herein incorporated by reference.

Polypeptide compositions of the isolated osteoinductive agents include, but are not limited to, isolated Bone Morphogenic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) or Transforming Growth Factor beta (TGF-beta707) polypeptides. Polypeptide compositions of the osteoinductive agents include, but are not limited to, full length proteins, fragments or variants thereof.

Variants of the isolated osteoinductive agents include, but are not limited to, polypeptide variants that are designed to increase the duration of activity of the osteoinductive agent in vivo. Typically, variant osteoinductive agents include, but are not limited to, full length proteins or fragments thereof that are conjugated to polyethylene glycol (PEG) moieties to increase their half-life in vivo (also known as pegylation). Methods of pegylating polypeptides are well known in the art (See, e.g., U.S. Pat. No. 6,552,170 and European Pat. No. 0,401,384 as examples of methods of generating pegylated polypeptides). In some embodiments, the isolated osteoinductive agent(s) are provided as fusion proteins. In one embodiment, the osteoinductive agent(s) are available as fusion proteins with the Fc portion of human IgG. In another embodiment, the osteoinductive agent(s) are available as hetero- or homodimers or multimers. Examples of some fusion proteins include, but are not limited to, ligand fusions between mature osteoinductive polypeptides and the Fc portion of human Immunoglobulin G (IgG). Methods of making fusion proteins and constructs encoding the same are well known in the art.

Isolated osteoinductive agents that are included within a matrix are typically sterile. In a non-limiting method, sterility is readily accomplished for example by filtration through sterile filtration membranes (e.g., 0.2 micron membranes or filters). In one embodiment, the matrix includes osteoinductive agents comprising one or more members of the family of Bone Morphogenic Proteins ("BMPs"). BMPs are a class of proteins thought to have osteoinductive or growth-promoting activities on endogenous bone tissue, or function as procollagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, isolated osteoinductive agents that are loaded in the matrix include osteoclastogenesis inhibitors to inhibit bone resorption of the bone tissue surrounding the site of implantation by osteoclasts. Osteoclast and osteoclastogenesis inhibitors include, but are not limited to, osteoprotegerin polynucleotides or polypeptides, as well as mature osteoprotegerin proteins, polypeptides or polynucleotides encoding the same. Osteoprotegerin is a member of the TNF-receptor superfamily and is an osteoblast-secreted decoy receptor that functions as a negative regulator of bone resorption. This protein specifically binds to its ligand, osteoprotegerin ligand (TNFSF11/OPGL), both of which are key extracellular regulators of osteoclast development.

Osteoclastogenesis inhibitors that can be loaded in the matrix further include, but are not limited to, chemical compounds such as bisphosphonate, 5-lipoxygenase inhibitors such as those described in U.S. Pat. Nos. 5,534,524 and 6,455,541 (the contents of which are herein incorporated by reference in their entireties), heterocyclic compounds such as those described in U.S. Pat. No. 5,658,935 (herein incorporated by reference in its entirety), 2,4-dioxoimidazolidine and imidazolidine derivative compounds such as those described in U.S. Pat. Nos. 5,397,796 and 5,554,594 (the contents of which are herein incorporated by reference in their entireties), sulfonamide derivatives such as those described in U.S. Pat. No. 6,313,119 (herein incorporated by reference in its entirety), or acylguanidine compounds such as those described in U.S. Pat. No. 6,492,356 (herein incorporated by reference in its entirety).

In another embodiment, isolated osteoinductive agents that can be loaded in the matrix include one or more members of the family of Connective Tissue Growth Factors ("CTGFs"). CTGFs are a class of proteins thought to have growth-promoting activities on connective tissues. Known members of the CTGF family include, but are not limited to, CTGF-1, CTGF-2, CTGF-4 polynucleotides or polypeptides thereof, as well as mature proteins, polypeptides or polynucleotides encoding the same.

In another embodiment, isolated osteoinductive agents that can be loaded in the matrix include one or more members of the family of Vascular Endothelial Growth Factors ("VEGFs"). VEGFs are a class of proteins thought to have growth-promoting activities on vascular tissues. Known members of the VEGF family include, but are not limited to, VEGF-A, VEGF-B, VEGF-C, VEGF-D, VEGF-E or polynucleotides or polypeptides thereof, as well as mature VEGF-A, proteins, polypeptides or polynucleotides encoding the same.

In another embodiment, isolated osteoinductive agents that can be loaded in the matrix include one or more members of the family of Transforming Growth Factor-beta ("TGFbetas"). TGF-betas are a class of proteins thought to have growth-promoting activities on a range of tissues, including connective tissues. Known members of the TGF-beta family include, but are not limited to, TGF-beta-1, TGF-beta-2, TGF-beta-3, polynucleotides or polypeptides thereof, as well as mature protein, polypeptides or polynucleotides encoding the same.

In another embodiment, isolated osteoinductive agents that can be loaded in the matrix include one or more Growth Differentiation Factors ("GDFs"). Known GDFs include, but are not limited to, GDF-1, GDF-2, GDF-3, GDF-7, GDF-10, GDF-11, and GDF-15. For example, GDFs useful as isolated osteoinductive agents include, but are not limited to, the following GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BCO30959, AAF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BCO28237 or AAH28237, as well as mature GDF-10 polypeptides or polynucleotides encoding the same.

GDF-11 polynucleotides or polypeptides corresponding to GenBank Accession Numbers AF100907, NP_005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP_004855, as well as mature GDF-15 polypeptides or polynucleotides encoding the same.

In another embodiment, isolated osteoinductive agents that can be loaded in the matrix include Cartilage Derived Morphogenic Protein (CDMP) and Lim Mineralization Protein (LMP) polynucleotides or polypeptides. Known CDMPs and LMPs include, but are not limited to, CDMP-1, CDMP-2, LMP-1, LMP-2, or LMP-3.

CDMPs and LMPs useful as isolated osteoinductive agents that can be loaded in the matrix include, but are not limited to, the following CDMPs and LMPs: CDMP-1 polynucleotides and polypeptides corresponding to GenBank Accession Numbers NM_000557, U13660, NP_000548 or P43026, as well as mature CDMP-1 polypeptides or polynucleotides encoding the same. CDMP-2 polypeptides corresponding to GenBank Accession Numbers or P55106, as well as mature CDMP-2 polypeptides. LMP-1 polynucleotides or polypeptides corresponding to GenBank Accession Numbers AF345904 or AAK30567, as well as mature LMP-1 polypeptides or polynucleotides encoding the same. LMP-2 polynucleotides or polypeptides corresponding to GenBank Accession Numbers AF345905 or AAK30568, as well as mature LMP-2 polypeptides or polynucleotides encoding the same. LMP-3 polynucleotides or polypeptides corresponding to GenBank Accession Numbers AF345906 or AAK30569, as well as mature LMP-3 polypeptides or polynucleotides encoding the same.

In another embodiment, isolated osteoinductive agents that can be loaded in the matrix include one or more members of any one of the families of Bone Morphogenic Proteins (BMPs), Connective Tissue Growth Factors (CTGFs), Vascular Endothelial Growth Factors (VEGFs), Osteoprotegerin or any of the other osteoclastogenesis inhibitors, Growth Differentiation Factors (GDFs), Cartilage Derived Morphogenic Proteins (CDMPs), Lim Mineralization Proteins (LMPs), or Transforming Growth Factor-betas (TGF-betas), as well as mixtures or combinations thereof.

In another embodiment, the one or more isolated osteoinductive agents that can be loaded in the matrix are selected from the group consisting of BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP- 18, or any combination thereof; CTGF-1, CTGF-2, CGTF-3, CTGF-4, or any combination thereof; VEGF-A, VEGF-B, VEGF-C, VEGF-D, VEGF-E, or any combination thereof; GDF-1, GDF-2, GDF-3, GDF-7, GDF-10, GDF-11, GDF-15, or any combination thereof; CDMP-1, CDMP-2, LMP-1, LMP-2, LMP-3, and/or any combination thereof; Osteoprotegerin; TGF-beta-1, TGF-beta-2, TGF-beta-3, or any combination thereof; or any combination of one or more members of these groups.

In some embodiments, BMP-2, BMP-7 and/or GDF-5 may be used at 1-2 mg/cc of matrix. The concentrations of growth factor can be varied based on the desired length or degree of osteogenic effects desired. Similarly, one of skill in the art will understand that the duration of sustained release of the growth factor can be modified by the manipulation of the compositions of the matrix, such as for example, microencapsulation of the growth factor within polymers. The sustained release matrix can therefore be designed to provide customized time release of growth factors that stimulate the natural healing process.

The growth factor may contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfate, sodium bisulfite, sodium thiosulfate, thimerosal, methylparaben, polyvinyl alcohol and phenylethyl alcohol; solubility adjusting agents; stabilizers; and/or cohesion modifiers. In some embodiments, the growth factor may comprise sterile and/or preservative free material.

These above inactive ingredients may have multi-functional purposes including the carrying, stabilizing and controlling the release of the growth factor and/or other therapeutic agent(s). The sustained release process, for example, may be by a solution-diffusion mechanism or it may be governed by an erosion-sustained process.

In some embodiments, a pharmaceutically acceptable formulation comprising a growth factor is provided, wherein the formulation is a freeze-dried or lyophilized formulation. Typically, in the freeze-dried or lyophilized formulation an effective amount of a growth factor is provided. Lyophilized formulations can be reconstituted into solutions, suspensions, emulsions, or any other suitable form for administration or use. The lyophilized formulation may comprise the liquid used to reconstitute the growth factor. Lyophilized formulations are typically first prepared as liquids, then frozen and lyophilized. The total liquid volume before lyophilization can be less, equal to, or more than the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored at or below 30° C., for example, refrigerated at 4° C., or at room temperature (e.g., approximately 25° C.).

Lyophilized formulations of the growth factor are typically reconstituted for use by addition of an aqueous solution to dissolve the lyophilized formulation. A wide variety of aqueous solutions can be used to reconstitute a lyophilized formulation. In some embodiments, lyophilized formulations can be reconstituted with a solution containing water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used. In some embodiments, the solutions do not contain any preservatives (e.g., are preservative free).

Application of the Growth Factor to the Matrix

In some embodiments, a therapeutic agent (including one or more growth factors) may be disposed on or in the interior of the matrix by hand, electrospraying, ionization spraying or impregnating, vibratory dispersion (including sonication), nozzle spraying, compressed-air-assisted spraying, injecting, brushing and/or pouring.

Application of the growth factor to the matrix may occur at the time of surgery or by the manufacturer or in any other suitable manner. For example, the growth factor may be further reconstituted using a syringe and the syringe can be placed into the interior of the matrix via insertion of a needle or cannula (piercing the matrix) and placing it into the interior of the matrix and injecting the growth factor so it is evenly distributed throughout the porous interior.

In some embodiments, the growth factor may be applied to the matrix (i.e., collagen) prior to combining the materials and forming it into the final matrix shape. Indeed, the growth factor can be blended into the natural or synthetic polymer (i.e., POE) and poured into molds of the final shape of the matrix. Alternatively, the growth factor, such as a bone morphogenetic protein in a suitable liquid carrier, may be applied onto and/or into the porous loaded matrix after forming it into the final shape by soaking, dripping, injecting, spraying, etc.

In some embodiments, the interior of the matrix is loaded with BMP that functions as an osteoinductive factor. Indeed, the preferred osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof.

Recombinant BMP-2 can be used at a concentration of about 0.4 mg/ml to about 10.0 mg/ml, preferably near 1.5 mg/ml. However, any bone morphogenetic protein is contemplated including bone morphogenetic proteins designated as BMP-1 through BMP-18. BMPs are available from Wyeth, Cambridge, Mass. and the BMPs and genes encoding them may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In some embodiments, the lyophilized growth factor (e.g., BMP) can be disposed in a vial by the manufacturer and then the surgeon can mix the diluent with the lyophilized growth factor. The matrix then can be parenterally administered to the target tissue site. The term "parenteral" as used herein refers to modes of administration which bypass the gastrointestinal tract, and include for example, intramuscular, intraperitoneal, intrasternal, subcutaneous, intra-operatively, intrathecally, intradiscally, peridiscally, epidurally, perispinally, intraarticular or combinations thereof.

The amount of growth factor, (e.g., bone morphogenic protein) may be sufficient to cause bone and/or cartilage growth. In some embodiments, the growth factor is rhBMP-2 and is contained in one or more matrices in an amount of from 1 to 2 mg per cubic centimeter of the biodegradable matrix. In some embodiments, the amount of rhBMP-2 morphogenic protein is from 2.0 to 2.5 mg per cubic centimeter (cc) of the biodegradable matrix.

In some embodiments, the growth factor is supplied in a liquid carrier (e.g., an aqueous buffered solution). Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the BMP-2 is provided in a vehicle (including a buffer) containing sucrose, glycine, L-glutamic acid, sodium chloride, and/or polysorbate 80.

In some embodiments, upon implantation of the matrix or components that contact the matrix (e.g., plugs that are separate from the matrix on implantation), compression of the matrix is reduced or eliminated. As discussed above, if unwanted compression occurs, this causes the buffer from the bone growth factor to leak from the matrix, which causes higher concentrations of the growth factor (e.g., 2 mg to 2.5 mg of rhBMP-2 per cc of matrix) to remain on the matrix. This high concentration of growth factor may lead to local transient bone resorption and excess osteoclast formation and bone breakdown. This may result in poor integration of the matrix with surrounding host tissue and a failed repair. Thus, by employing a compression resistant matrix, unwanted leakage is reduced or avoided. In some embodiments, localized release of the growth factor may cause local irritation to the surrounding tissue. In some embodiments, the leaking of growth factor from the matrix may reduce a stable microenvironment for new bone and/or cartilage growth. It also may cause the matrix to fail to retain its full efficacy over time to maximally promote bone growth at a target site.

Additional Therapeutic Agents

The growth factors of the present application may be disposed on or in the matrix with other therapeutic agents. For example, the growth factor may be disposed on or in the carrier by electrospraying, ionization spraying or impregnating, vibratory dispersion (including sonication), nozzle spraying, compressed-air-assisted spraying, brushing and/or pouring.

Exemplary therapeutic agents include but are not limited to IL-1 inhibitors, such Kineret® (anakinra), which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. Interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), and aurin-tricarboxylic acid (which inhibits TNF-α), may also be useful as therapeutic agents for reducing inflammation. It is further contemplated that where desirable a pegylated form of the above may be used. Examples of still other therapeutic agents include NF kappa B inhibitors such as antioxidants, such as dithiocarbamate, and other compounds, such as, for example, sulfasalazine.

Examples of therapeutic agents suitable for use also include, but are not limited to, an anti-inflammatory agent, analgesic agent, or osteoinductive growth factor or a combination thereof. Anti-inflammatory agents include, but are not limited to, apazone, celecoxib, diclofenac, diflunisal, enolic acids (piroxicam, meloxicam), etodolac, fenamates (mefenamic acid, meclofenamic acid), gold, ibuprofen, indomethacin, ketoprofen, ketorolac, nabumetone, naproxen, nimesulide, salicylates, sulfasalazine [2-hydroxy-5-[-4-[C2-pyridinylamino)sulfonyl]azo]benzoic acid, sulindac, tepoxalin, and tolmetin; as well as antioxidants, such as dithiocarbamate, steroids, such as cortisol, cortisone, hydrocortisone, fludrocortisone, prednisone, prednisolone, methylprednisolone, triamcinolone, betamethasone, dexamethasone, beclomethasone, fluticasone or a combination thereof.

Suitable analgesic agents include, but are not limited to, acetaminophen, bupivicaine, fluocinolone, lidocaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, mepiridine, methadone, morphine, nalbuphine, opium, oxycodone, papavereturn, pentazocine, pethidine, phenoperidine, piritramide, dextropropoxyphene, remifentanil, tilidine, tramadol, codeine, dihydrocodeine, meptazinol, dezocine, eptazocine, flupirtine, amitriptyline, carbamazepine, gabapentin, pregabalin, or a combination thereof.

In some embodiments, a statin may be used. Statins include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

Kits

The matrix, growth factor and devices to administer the implantable matrix composition may be sterilizable. In various embodiments, one or more components of the matrix, and/or medical device to administer it may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the implantable matrix may be packaged in a moisture resistant package and then terminally sterilized by gamma irradiation. In use the surgeon removes the one or all components from the sterile package for use.

In various embodiments, electron beam (e-beam) radiation may be used to sterilize one or more components of the matrix. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the implantable matrix and/or one or more components of the matrix, including, but not limited to, gas sterilization, such as, for example, with ethylene oxide or steam sterilization.

In various embodiments, a kit is provided comprising the growth factor, matrix, and/or diluents. The kit may include additional parts along with the implantable matrix combined together to be used to implant the matrix (e.g., wipes, needles, syringes, etc.). The kit may include the matrix in a first compartment. The second compartment may include a vial holding the growth factor, diluent and any other instruments needed for the localized drug delivery. A third compartment may include gloves, drapes, wound dressings and other procedural supplies for maintaining sterility of the implanting process, as well as an instruction booklet, which may include a chart that shows how to implant the matrix after reconstituting the growth factor. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implantable matrix configured to fit at or near a target tissue site, the matrix comprising: a biodegradable polymer and a plurality of elongated particles embedded within the polymer, the elongated particles embedded in the polymer uniformly or randomly so as to reduce compression of the matrix, wherein the matrix includes a plurality of pores between about 50 µm and 500 µm and has a porosity of at least 30% such that the matrix allows influx of at least progenitor, bone and/or cartilage cells therein, wherein the elongated particles comprise tricalcium phosphate and hydroxyapatite in a ratio of about 80:20 to about 90:10, and the elongated particles represent at least 50 to 98 weight percent of the matrix.

2. An implantable matrix according to claim 1, wherein (i) compression of the matrix is reduced by at least 10% when a load bearing force is applied to the matrix or (ii) the plurality of elongated particles overlap and contact each other in the matrix.

3. An implantable matrix according to claim 1, wherein compression of the matrix is reduced by at least 20% when a load bearing force is applied to the matrix.

4. An implantable matrix according to claim 1, wherein (i) the elongated particles have a modulus of elasticity of between 2 MPa and 100 MPa or (ii) the purality of elongated particles are entangled in the matrix.

5. An implantable matrix according to claim 1, wherein the matrix and elongated particles are resorbable and facilitate or accelerate new bone growth by at least one of osteogenesis, osteoconduction and osteoinduction.

6. An implantable matrix according to claim 1, wherein the elongated particles further comprise a resorbable ceramic, bone, a degradable synthetic polymer, hyaluronic acid, chitosan or combinations thereof.

7. An implantable matrix according to claim 1, wherein the elongated particles comprise tricalcium phosphate and hydroxyapatite in a ratio of about 85:15.

8. An implantable matrix according to claim 1, wherein the elongated particles are not aggregated.

9. An implantable matrix according to claim 1, wherein the elongated particles further comprise bone particles obtained from cortical, cancellous, corticocancellous, allogenic, xenogenic or transgenic bone tissue.

10. An implantable matrix according to claim 1, wherein the median length of the elongated particles is from about 2 to about 20 mm, the median width of the elongated particles is from about 0.02 to about 5 mm and the ratio of median length to median width is from about 10:1 to about 1000:1.

11. An implantable matrix according to claim 1, wherein the median length of the elongated particles is from about 1 to about 10 mm, the median width of the elongated particles is from about 0.04 to about 2 mm and the ratio of median length to median width is from about 20:1 to about 200:1.

12. An implantable matrix according to claim 1, wherein the elongated particles further comprise bone powder, demineralized bone powder, porous calcium phosphate ceramics, bioactive glass or a combination thereof.

13. An implantable matrix according to claim 1, wherein the matrix is in the form of a bi-layered sponge, plug, pin, peg, or cylinder and further comprises autograft, allograft or xenograft progenitor, bone and/or cartilage cells seeded within the matrix.

14. An implantable matrix according to claim 1, wherein the matrix comprises a growth factor comprising bone morphogenic protein-2 and the matrix comprises collagen.

15. An implantable matrix according to claim 1, wherein the matrix comprises collagen, the elongated particles are uniformly embedded in the polymer, and a growth factor comprising BMP-2 is disposed on or in the matrix.

16. An implantable matrix configured to fit at or near a target tissue site, the matrix comprising: collagen and a plurality of elongated mineral particles embedded within the collagen, the elongated mineral particles embedded in the collagen uniformly or randomly so as to reduce compression of the matrix, wherein the matrix includes a plurality of pores between about 50 µm and 500 µm and has a porosity of at least 30% such that the matrix allows influx of at least progenitor, bone and/or cartilage cells therein; and the matrix comprises bone morphogenic protein, herein the elongated particles comprise tricalcium phosphate and hydroxyapatite in a ratio of about 80:20 to about 90:10, and the elongated particles represent at least 50 to 98 weight percent of the matrix.

* * * * *